United States Patent
Beauducel

(12) 
(10) Patent No.: US 6,239,877 B1
(45) Date of Patent: May 29, 2001

(54) POLARIZED INTERFERENTIAL MEASUREMENT WHEREIN THE MODULATION SIGNAL IS ADJUSTED TO BE EQUAL TO THE DURATION OF THE MEASUREMENT WINDOW

(75) Inventor: Claude Beauducel, Henonville (FR)

(73) Assignee: Institut Francais du Petrole, Rueil-Malmaison cedex (FR)

(*) Notice: Subject to any disclaimer, the term of this patent is extended or adjusted under 35 U.S.C. 154(b) by 0 days.

(21) Appl. No.: 09/236,603

(22) Filed: Jan. 26, 1999

(30) Foreign Application Priority Data

Jan. 28, 1998 (FR) .................................................. 98 00931

(51) Int. Cl.$^7$ ........................................................ G01B 9/02
(52) U.S. Cl. .......................... 356/484; 356/491; 356/517
(58) Field of Search .................................... 356/349, 351, 356/361, 484, 491, 517, 453

(56) References Cited

U.S. PATENT DOCUMENTS

| | | | |
|---|---|---|---|
| 3,700,334 | * 10/1972 | Low et al. | ............................ 356/351 |
| 4,787,746 | 11/1988 | Couillaro | ............................ 356/361 |
| 5,483,344 | 1/1996 | Frot et al. | ............................ 356/361 |
| 5,619,329 | 4/1997 | Otani . | |
| 5,710,630 | 1/1998 | Essenpaeis et al. | ................. 356/346 |

* cited by examiner

*Primary Examiner*—Samuel A. Turner
(74) *Attorney, Agent, or Firm*—Antonelli, Terry, Stout & Kraus, LLP

(57) ABSTRACT

The invention is an interferential refractometry method and device using fine measurement of the displacement of the fringes of an interference pattern between two light beams with one of the beams undergoing phase variations due to variations in the refractive index thereof. The method comprises application, to one of the two beams, of a relatively fast periodic phase modulation by a modulating signal. Displacement of the fringes resulting from the combined application of the two modulations is picked up by a photodetector and a measuring system evaluates the slow modulation by determining the frequency spectrum of the signal coming from the detect or and measuring the phase shift affecting the fundamental frequency of this frequency spectrum. The method may be applied to detection of variations in the composition of mixtures, for example in analytical or preparative chromatography.

43 Claims, 6 Drawing Sheets

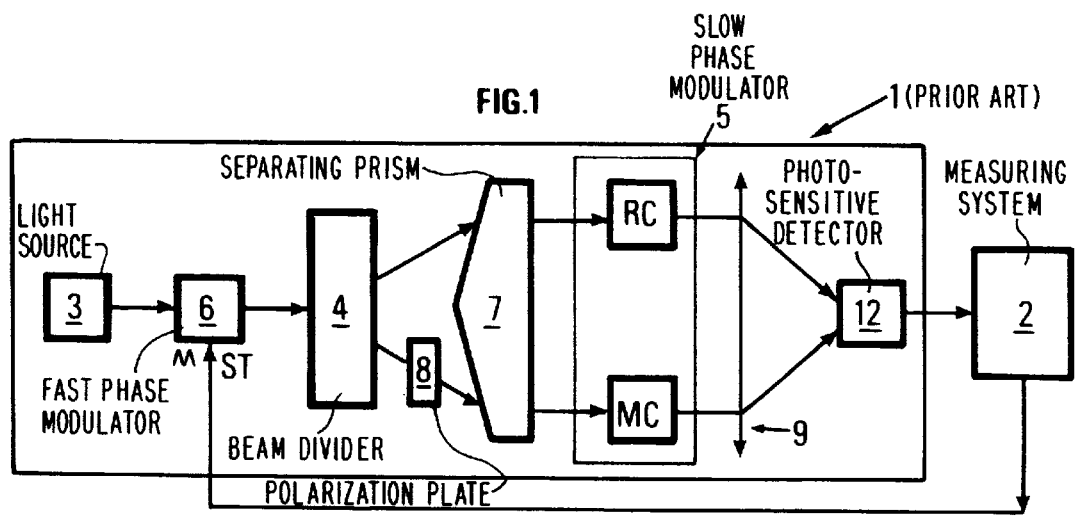
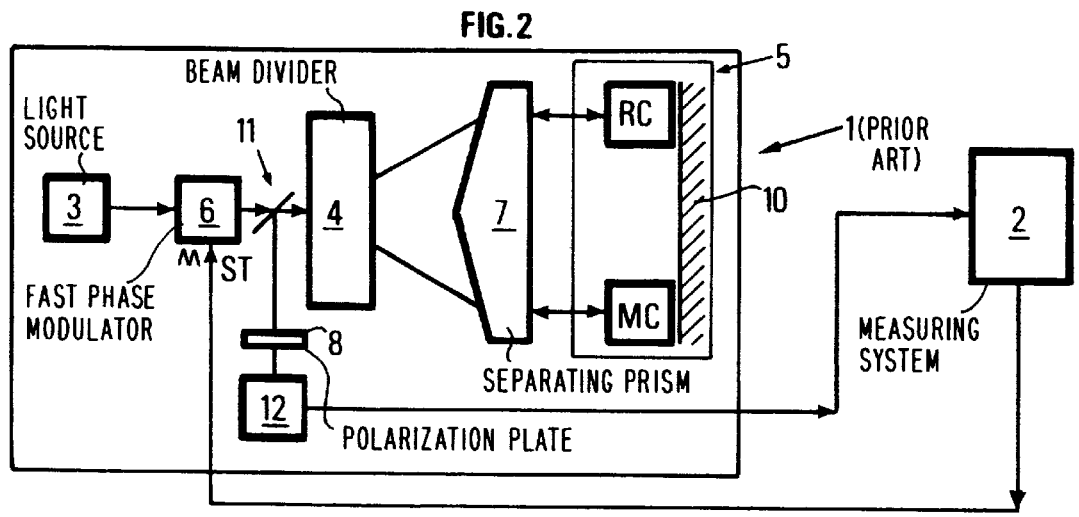
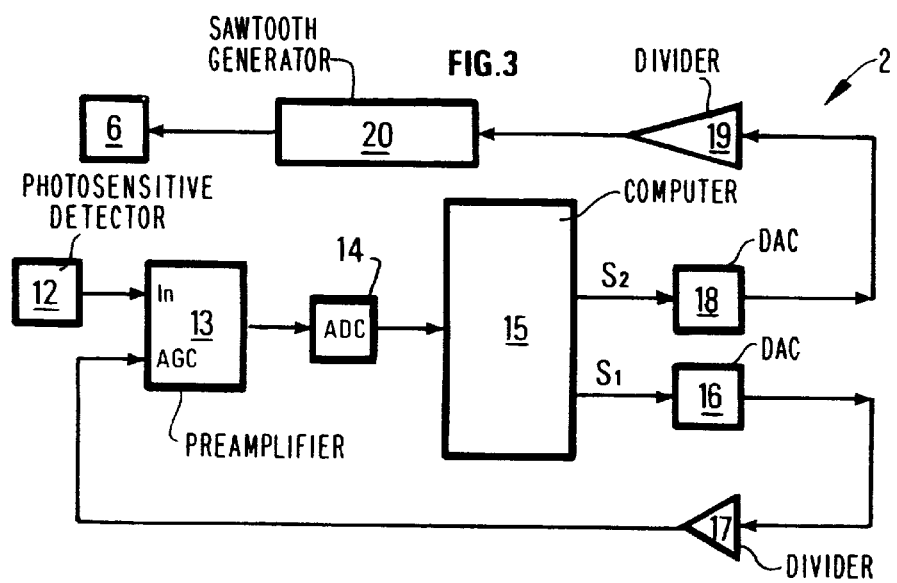

| | Fundamental Sign | Harmonic Sign |
|---|---|---|
| Period >window | + | + |
| | - | - |
| Period >window | + | - |
| | - | + |

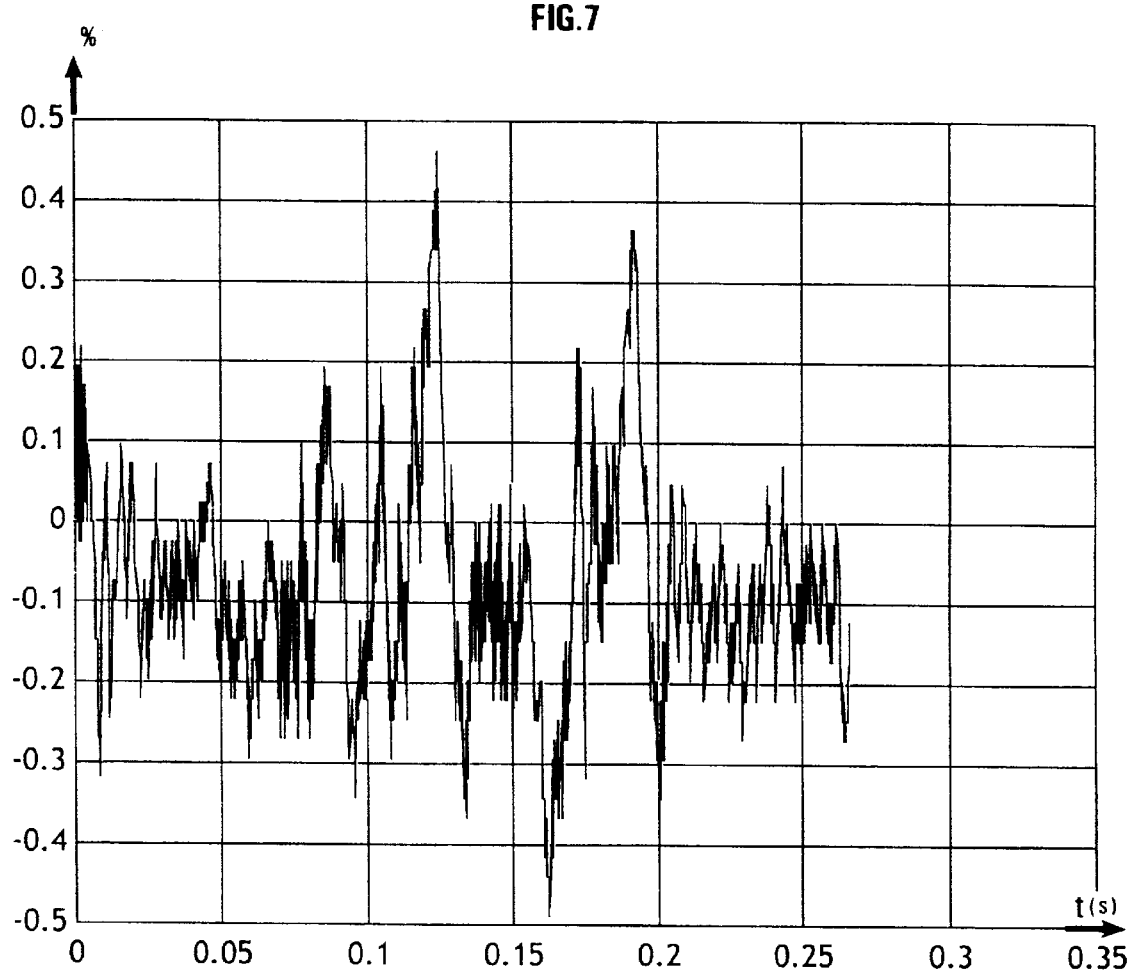

POLARIZED INTERFERENTIAL MEASUREMENT WHEREIN THE MODULATION SIGNAL IS ADJUSTED TO BE EQUAL TO THE DURATION OF THE MEASUREMENT WINDOW

BACKGROUND OF THE INVENTION

1. Field of the Invention

The present invention relates to a method and to a device provided for interferential measurement of the phase shift between two light beams coming from the same polarized source by fine measurement of the displacement of the fringes of an interference pattern between two light beams, one of the beams undergoing phase variations due to variations in the refractive index thereof, such as applied refractometry.

2. Description of the Prior Art

Among the various known refractometer types, there is the working with a monochromatic source whose beam is divided so as to pass concurrently through two tanks, one for the reference liquid and the other for the medium to be analysed, and with means for gathering the two beams together and for lighting a photodetector. Interferences, occuring because of the variation of the optical path resulting from the index variation and the intensity variations due to the displacement of the interference fringes, are measured.

French Patent 2,596,526 illustrates an example of refractometric detector in which each one of the (reference and measuring) tanks is independently part of an interferometry system, both tanks being supplied with light by the same source. Detection is achieved by two independent photodetectors which thus receive each a luminous intensity which sinusoidally varies as a function of the difference in the refractive indices between the reference tank or the measuring tank on the one hand and the air on the other. Individual calibration of each photometer is thus necessary. This optical system comprises a piezoelectric element designed to vibrate a mirror on which part of the light beam coming from the source reflects.

French Patent 2,697,336 describes a modulated phase type refractometer in which two beams that have passed respectively through a reference cell and a cell containing a medium whose refractive index undergoes variations are caused to interfere with each other. The two beams are formed from a single beam emitted by a laser after passing through a Pockels cell to which a fast alternating voltage suited to oscillate the interference pattern is applied, such as a sawtooth signal (FIG. 1) whose frequency is of the order of several KHz and whose amplitude is sufficient to obtain a displacement greater than 1.5 fringe (FIG. 2). The result on the interference pattern is the superposition of a slow variation linked with the composition variation of the medium and of a faster oscillating variation at the frequency of the alternating voltage. The intensity variations due to the fringe displacements are measured by a photometer and applied to electronics which converts the variations to logical signals and measurement of the phase shift between the cell control signal and the modulated intensity signals by counting by means of a clock signal. When the refractive index of the medium does not change, the output signal of the measuring phototransistor is that shown in FIG. 2.

The previous system eliminates many sources of inaccuracy of the prior systems insofar as the two interfering beams both come from the Pockels cell and therefore have the same optical <<past>>. However, for several reasons notably linked with the method used for measuring time lags between signal fronts, it appears that the accuracy that can be obtained (several %) can be considered insufficient for certain applications, notably in the field of chromatography.

SUMMARY OF THE INVENTION

The interferential method according to the invention greatly improves the accuracy that can be obtained when measuring the phase shift between two light beams coming from the same polarized source, when one of the beams undergoes a relatively slow phase variation and one of the two beams is subjected to a relatively fast periodic phase modulation by a modulating signal. The method comprises fine measurement of the displacement of the fringes of an interference pattern formed by causing the two beams to interfere with each other, picked up by a photodetector sensitive to the luminous intensity variation resulting from the displacement of the interference fringes.

The method can be used in many fields, notably in order to determine for example refractive index variations concomitant with variations in the composition of a medium studied, in relation to a reference medium.

The method can be used notably in the field of high-performance liquid chromatography, referred to as HPLC, either analytical or preparative, where it is important to know the composition of mixtures with high precision.

The method comprises determining the frequency spectrum of the signal coming from the detector and measuring the phase shift (by calculating the complex argument thereof for example) that affects the fundamental frequency of this frequency spectrum.

The method can be advantageously applied to interferential refractometry operations where the slow phase modulation is the result of a refractive index variation of a medium.

According to an embodiment, the frequency spectrum is formed from a signal portion coming from the photodetector and included in a measuring window substantially equal (and preferably really equal) to at least one period of the modulating signal, and the period of the modulating signal is therefore preferably controlled by the duration selected for the measuring window.

The amplitude of the signal detected by the photodetector is also preferably adjusted so that the analog-to-digital converter always works at full scale despite possible transparency variations of the zell containing the medium studied.

In order to improve the accuracy of the results even further, the phase shift measurements can be performed separately on distinct fractions of the fast modulation signal.

The device according to the invention comprises an optical instrument including an optical system which generates two beams from the same light source, phase shifters which modulate one of the two beams where a relatively slow phase variation and which modulates one of the two beams with a relatively fast periodic phase modulation, a device which causes the two beams to interfere with each other and a photodetector for detecting the displacement of the fringes of the interference pattern formed from the two beams. The device comprises a system which determines the frequency spectrum of the signal coming from the photodetector and which measures the phase shift that affects the fundamental frequency of this frequency spectrum.

The device according to the invention can be applied to interferential refractometry operations. The phase-shifter which modulates one of the beams to a relatively slow phase modulation in relation to that of the other beam comprises at least one cell containing a medium whose refractive index varies (in correlation with variations in the composition thereof for example), the phase shifter for modulating one of the two beams with to a relatively fast phase modulation comprises a cell suited to dephase the light under the action of a periodic modulation voltage applied thereto, and the electronic system comprises a computer programmed to carry out a fast Fourier transform (FFIT) on the signals coming from the detector during a fixed time interval and to determine the phase shift that affects the fundamental component of the spectrum.

The device preferably comprises a means for permanently adjusting the period of the modulation voltage to the time interval duration, this means being for example a computers combining the respective signs of the harmonic phases and the sign of the fundamental frequency in order to generate a correction signal.

The device preferably comprises an automatic gain control which controls the amplification gain applied to the signals from the photodetector.

According to a particular embodiment, the device comprises an amplifier which amplifies the signal coming from the photodetector, a the amplified signal during an acquisition time interval, a signal generator which periodically controlsthe second phase, a computer programmed to carry out a fast Fourier transform (FFT) on the signals coming from the detector during a time interval, which determines the phase shift affecting the fundamental component and which provides a first signal which controls the gain of the amplifier, and a second signal which controls the period of the signal produced by the generator is by the duration of the acquisition time interval, by combining for example the respective signs of the harmonic phases and the sign of the fundamental frequency.

The process and the device according to the invention are advantageous by reducing the residual error when measuring the phase variation (reduced by a factor of the order of 20 to 30) in relation to that obtained with the prior art.

BRIEF DESCRIPTION OF THE DRAWINGS

Other features and advantages of the process according to the invention will be clear from reading the description hereafter of a non limitative embodiment example, with reference to the accompanying drawings wherein FIG. 1 shows a first prior art embodiment example of a device which measures the refractive index variation of a transparent mixture in a cell by comparison with a stable reference medium, FIG. 2 shows a second prior art embodiment example of the device in the same refractometry application, FIG. 3 diagrammtically shows an electronic system for measuring the phase variations affecting the signals received by the photodetector, FIGS. 4a and 4b respectively show the relative amplitude A of the various lines n of the frequency spectrum of the signals received and their respective phases $\phi$ expressed in radians in a case where the fast modulation period $T_{SW}$ is greater than the duration $T_W$ of the measuring window of these signals, FIGS. 5a and 5b respectively show the relative amplitude A of the various lines n of the frequency spectrum of the signals received and their respective phases $\phi$ expressed in radians in a case where the fast modulation period $T_{SW}$ is less than the duration $T_W$ of the measuring window of these signals, FIG. 7 shows the (permanently corrected) variation of the difference $\Delta t$ that can be found between the modulation period $T_{SW}$ and the duration $T_W$ of the window, FIG. 8 show, as a function of time, the adjustment curve of the gain G of the preamplifier after an initial shift of the order of 20%.

DETAILED DESCRIPTION OF THE INVENTION

Figure 4B:
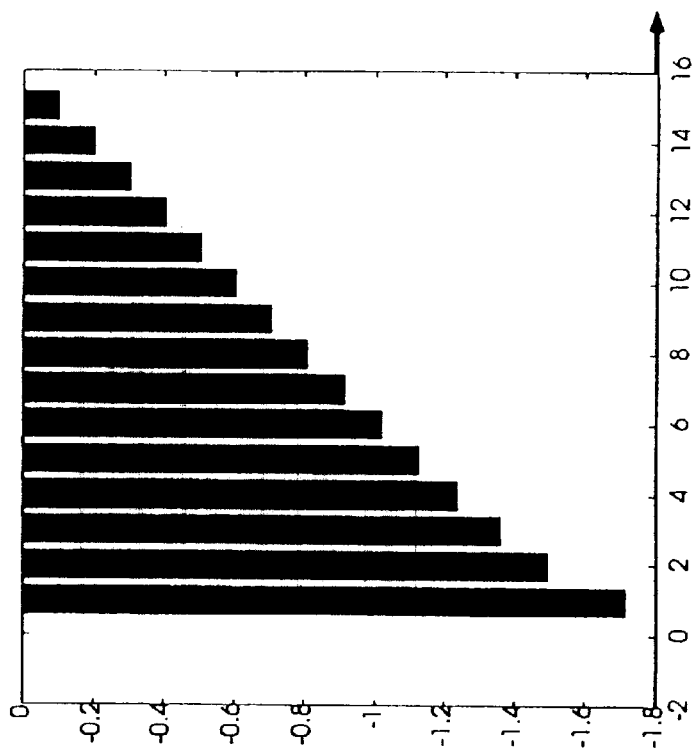

FIGS. 1 and 2 illustrate a prior art apparatus 1 for forming an interference pattern which has for example the same functionalities as the device described in the aforementioned French Patent 2,596,526 and that are reminded an associated measuring system 2.

This device comprises a source 3 emitting a preferably coherent polarized light beam, beam divider 4 for dividing the beam emitted by the source into two beams, a first slow phase shift modulator means 5 interposed on the path of one of the two beams, which subjects it to a first slow phase modulation in relation to the other beam. this phase modulator 5 for example is a first cell MC containing a transparent mixture to be analysed, whose refractive index changes in correlation with changes in the composition thereof, and of a second cell RC containing another transparent mixture of invariable composition and therefore invariable refractive index. A second fast phase modulator designed for fast phase shift of the phase of a beam, such as a Pockels type birefrigent cell for example to which a sawtooth modulation voltage V of period T is applied (by means of a transformer that is not shown), is interposed on the path of the light coming from source 3.

The output of beam divider 4 is applied to a beam separator 7 which may be for example of a Wollaston type beam separating prism. The Pockels cell 6 and separating prism 7 are suitably oriented in relation to each other and both in relation to the direction of polarization of the beam coming from light source 3, so that the intensity of the two beams is substantially equal and that only one of the beams is affected by the fast modulation applied by cell 6. A means is used for forming an interference pattern of the two beams coming from the first and second phase-shifting means.

According to the embodiment of FIG. 1, this means comprises a birefringent prism 7 associated with a polarization plate 8 which brings the two beams back into the same polarization plane, and with convergent lenses 9.

According to the embodiment of FIG. 2, the means for forming the interference pattern of the two beams comprises a mirror 10 (made by metallization of the rear faces of cells MC and RC), a semireflecting plate 11 placed between birefringent cell 6 and the Wollaston prism 4 for sending the beams back towards polarization plate 8 and allowing interference of the beams.

A photosensitive detector 12 is placed downstream from lenses 9 (FIG. 1) or downstream from semireflecting plate 11 and phase plate 8 (FIG. 2) in the plane of formation of the interference fringes between the two beams. It detects the luminous intensity variations resulting from the displacement of the interference fringes concomitant with the slow modulation and the fast modulation applied to either of the interfering beams.

The apparatus 1 is connected to electronic measuring system 2 that measures the slow phase shifts resulting from the slow refractive index variation of the medium to be studied in cell MC and which generates a control signal for the fast phase modulator 6.

The measurement principle basically uses a fast Fourier transform (FFT), in determining the frequency spectrum associated with the digitized signal and in determining the phase shift that affects the complex principal component (or fundamental) of the spectrum by calculating the argument of this component.

Electronic measuring system 2 comprises an adapter preamplifier 13 connected to photodetector 12. The signal amplified by preamplifier 13 is applied to an analog-to-digital converter (ADC) 14 which samples it and digitizes the successive samples taken with a determined sampling interval, in a measuring window of duration T.

The digitized samples are stored in a microcomputer 15 comprising for example a digital signal processor (DSP) programmed to carry out a fast Fourier transform (FFT) from the digitized data and which measures the phase shift affecting the complex fundamental component of the frequency spectrum of the signal.

As explained hereunder, microcomputer 15 produces a first digital signal S1 that is applied to a first digital-to-analog converter (DAC) combined with a first voltage divider 17. The resulting signal is applied in counterreaction to preamplifier 13 at the gain control input (AGC) thereof. The output signal of the photodetector, having an amplitude varying according to the refractive index of the sample to be measured, has a gain applied which is adapted to the measuring signals so that analog-to-digital converter 14 permanently works at full-scale.

Similarly, the microcomputer is producing a second digital signal S2 that is applied to a second digital-to-analog converter 18 (DAC) combined with a second voltage divider 19. The resulting signal is applied to a control input of a sawtooth voltage generator 20 which produces the fast modulation signal $S_T$ of birefringent cell 6 (FIGS. 1 and 2). It has the effect of causing the period $T_{SW}$ of the sawtooth to be permanently and precisely controlled by the duration $T_W$ of the sampling window of converter 14.

Precise control is obtained by means of a phase calculation relative to the respective phases of the fundamental frequency and of the harmonics of the calculated frequency spectrum.

Figure 4A:
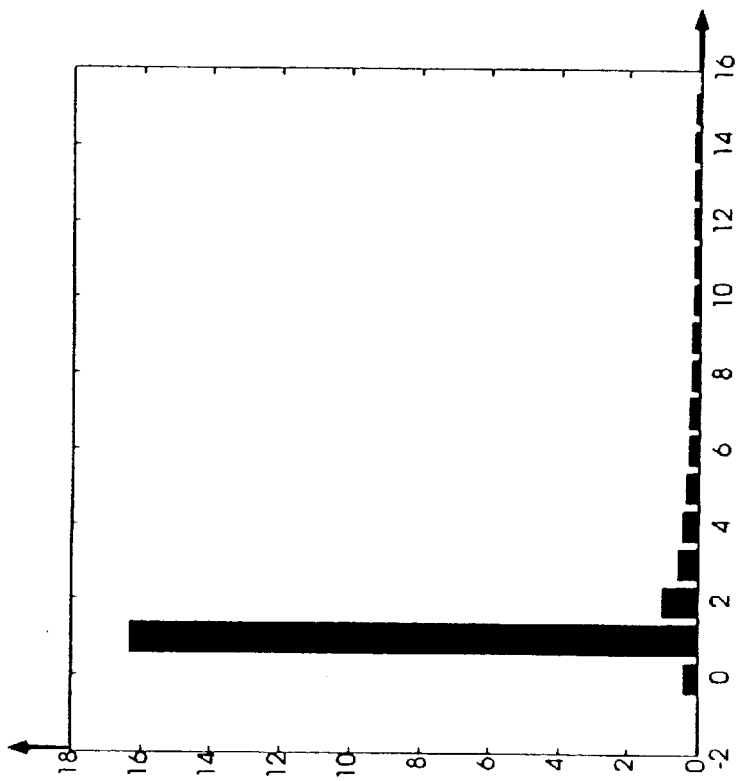
Figure 5B:
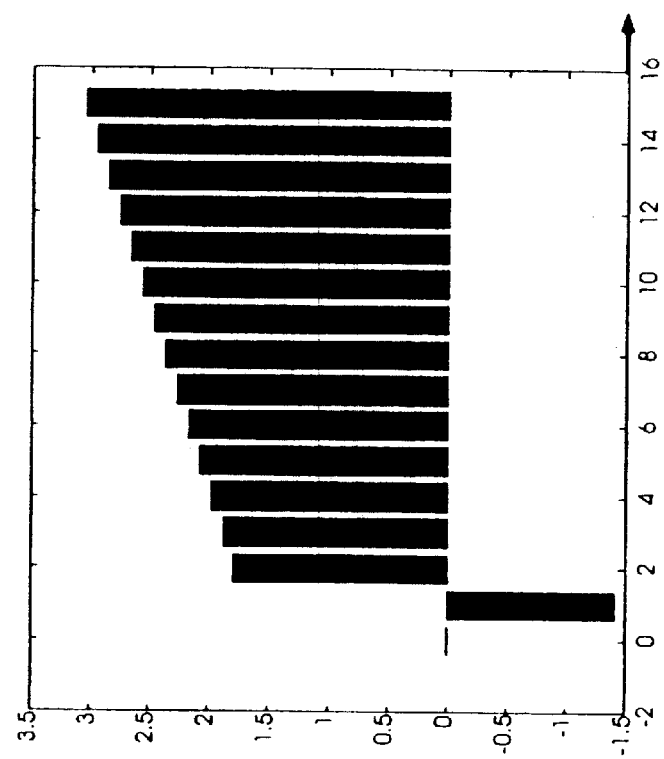
Figure 5A:
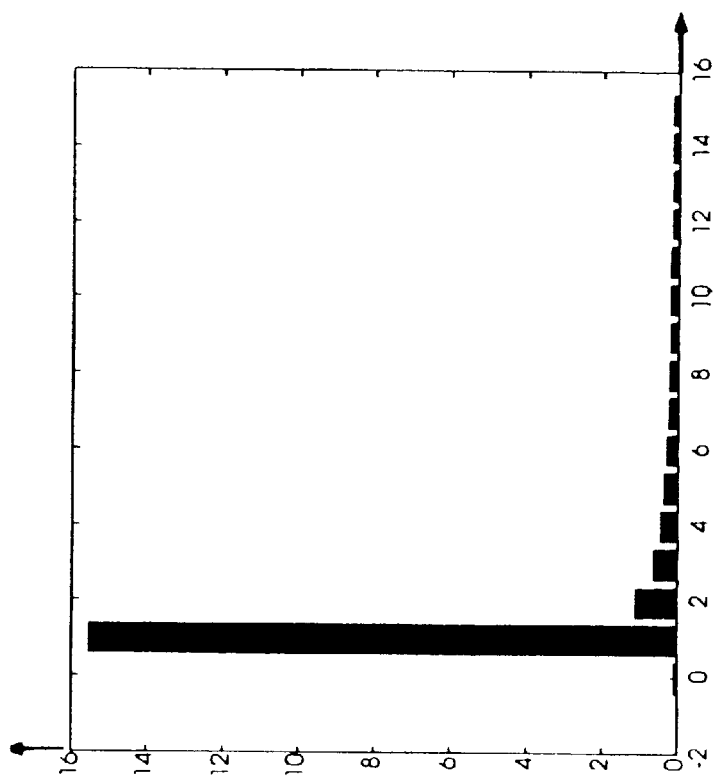

If the spectrum of the measuring signal coming from photodetector 12 is determined by FFT when period $T_{ST}$ is different from the duration $T_W$ of the window, it can be observed that a) the amplitude of the various lines varies with the difference (FIGS. 4a and 5b on the one hand) and that b) their phase undergoes a sudden discontinuity when the difference between them changes direction, as illustrated by FIGS. 4b and 5b.

Figures 6, 8:
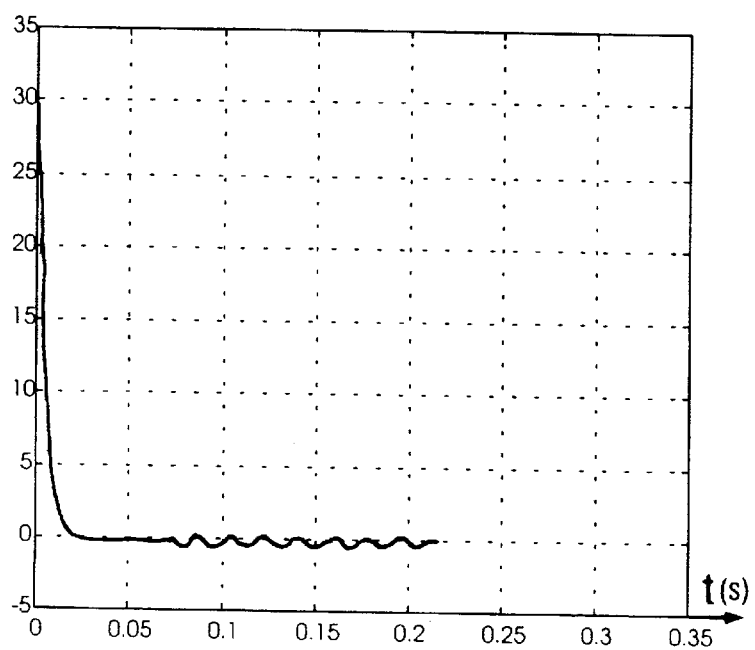
FIG. 6 shows a table illustrating the computation carried out in order to determine the direction of adjustment of the fast modulation period $T_{SW}$ and of the duration $T_W$ of the measuring window according to the respective signs $S_F$ and $S_H$ of the fundamental F and of the harmonics H.

When period $T_{ST}$ is greater than the duration $T_W$ of the window (FIG. 4b), the phase of the harmonics has the same direction as that of the fundamental, whereas it has an opposite direction when period $T_{ST}$ is shorter (FIG. 5b). The table of FIG. 6 shows an analysis of the respective phase directions of the fundamental and of the various harmonics.

The sign change of the harmonics phase occurs with very slight period errors depending on the calculation accuracy of the FFT. For example, in case of a FFT transform carried out with 32 sampling points in window $T_W$ with an 8-bit digitization, a relative period error below $3.10^{-4}$ can be detected.

The signal S1 applied at the gain control input (AGC) of preamplifier 13 (FIG. 3) is computed by the microcomputer from the value of the amplitude of the fundamental, then it is integrated digitally. FIG. 8 shows the correction efficiency obtained with an initial gain difference of 20% in relation to the optimum gain.

In order to generate the correction signal S2 allowing control of the period $T_{ST}$ of the sawtooth voltage, microcomputer 15 is suited to sum the signs of the angles of the harmonics and to multiply the result by the sign of the angle of the fundamental. These signs are readily obtained by taking those of the imaginary part of the result of the FFT calculation. This resulting error signal is integrated digitally and applied to converter 18 (FIG. 3), then to ramp generator 20. The efficiency of the control obtained can be seen in FIG. 7.

Figure 9:
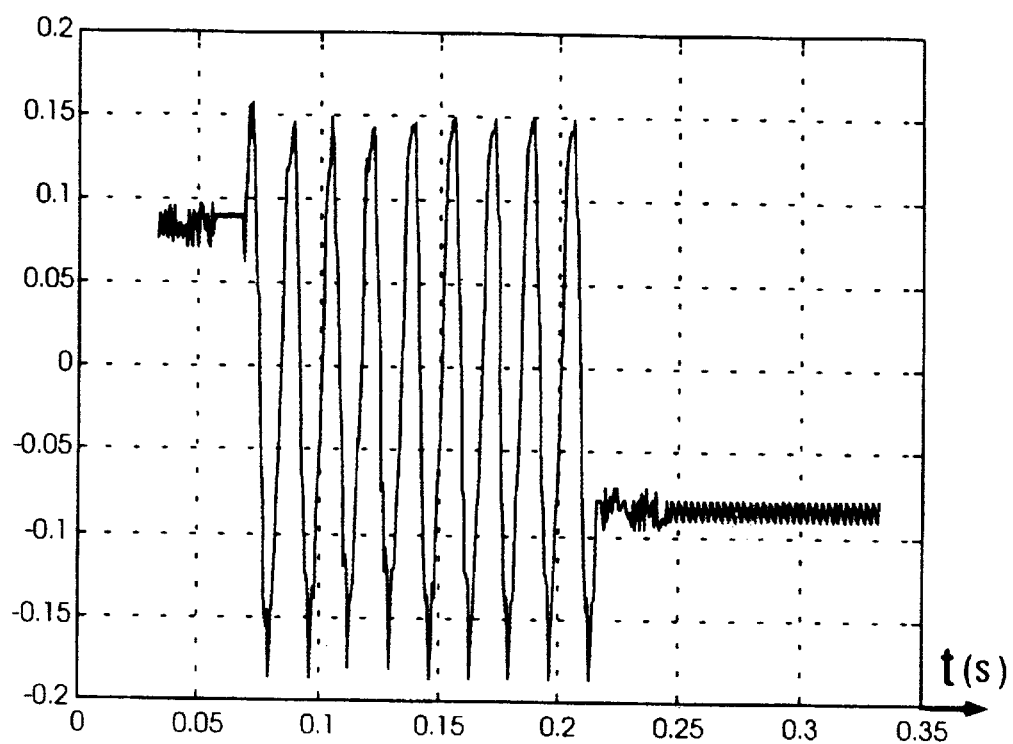
FIG. 9 shows that the absolute error in percentage for the width of a fringe $\Delta l$ made with the method according to the invention lies within very narrow limits.

The method of measuring the refractive index variation due to the composition variation of the medium in measuring cell MC, which is implemented by the device, considerably improves the accuracy that can be obtained, as shown in FIG. 9. In fact, it can be seen that the phase error is of the order of 0.3% peak to peak in percentage of the width of a fringe, i.e. a gain of nearly 20 dB (which represents a factor of the order of 30) in relation to the results of the prior method, with a nearly sinusoidal variation of the error as a function of the fractional phase.

It can seen that the device is much less sensitive to disturbances of electric origin and to signal distortions since the phase measurement is integrated in the whole measuring window.

Maintenance of the period $T_{ST}$ of the electric control voltage applied to the birefringent Pockels cell 6 that has the same duration as the acquisition window $T_W$ of the measuring signals coming from photodetector 12 has the positive effect of substantially decreasing the amplitude of the necessary control voltage and therefore of decreasing the stresses undergone thereby.

The gain control system also allows continuous knowledge of the amplitude of the signal coming from the photodetector. Anomalies such as the presence of impurities or of bubbles can therefore be readily noticed and small reliable measurements can thus be detected.

The previous results can be appreciably improved by calculating separately the fractional phases measured on the <<ascending>> and <<descending>> parts of the excitation signal of cell 6 (FIGS. 1 and 2) and by calculating the average thereof.

Examples of application of the method to refractometry have been described. The method according to the invention can however be applied more generally to the fine detection of phase shifts between interfering beams without departing from the scope of the invention.

What is claimed is:

1. An interferential method for measuring phase shift between two light beams coming from a single polarized source wherein one of the beams undergoes a slower phase variation and another of the beams undergoes faster periodic phase variation produced by a modulating signal having an adjustable period by a measurement of displacement of fringes of an interference pattern formed by interference of the two light beams which produces displacement of the interference fringes which is detected by a photodetector, said method comprising:

adjusting the period of the modulating signal to be substantially in duration equal to a duration of a measuring window;

determining a frequency spectrum of a portion of a signal sensed by the photodetector during the measuring window; and measuring a phase shift affecting a fundamental frequency of the frequency spectrum.

2. A method as claimed in claim 1 comprising:
using the measured phase shift on distinct fractions of the faster periodic phase variations.

3. A method as claimed in claim 1 wherein:
the measurement of the phase shift is performed by calculating a complex fundamental component of the fundamental frequency.

4. A method as claimed in claim 2 wherein:
the measurement of the phase shift is performed by calculating a complex fundamental component of the fundamental frequency.

5. A device for measuring phase shift between two light beams coming from a single polarized source, comprising:

an optical system which generates two beams from a single light source, a first phase-shifter which applies to one of the light beams a slower phase variation and a second phase-shifter which applies to another of the light beams a faster periodic phase variation with an adjustable period, at least one optical device which produces an interference between the two light beams, a photodetector which detects the displacement of fringes of an interference pattern formed from interference of the two light beams, and a control which adjusts a period of the faster periodic phase variation to be substantially in duration equal to a duration of a measuring window; and a processor which determines a frequency spectrum of a portion of a signal produced by the photodetector measured during the measuring window and measures a phase shift affecting a fundamental frequency of the frequency spectrum.

6. An interferential refractometry device comprising:

a source producing a polarized light beam, a divider which divides the polarized light beam into two polarized light beams, a first phase shifter which subjects one of the polarized light beams to a first slower phase modulation, a second phase which subjects another of the polarized beams to a faster phase modulation under control of a modulating signal, at least one optical device which produces an interference pattern between the two polarized light beams outputted from the first and the second phase-shifters and a photodetector which senses an intensity variation resulting from a displacement of interference fringes produced by the phase modulations and a control which adjusts a period of the modulating signal to be substantially in duration equal to a duration of a measuring window; and a processor which determines a frequency spectrum of a portion of a signal produced by the photodetector measured during the measuring window and measures a phase shift affecting a fundamental frequency of the frequency spectrum.

7. A device as claimed in claim 6, wherein:
the first phase-shifter comprises at least one cell containing a medium having a refractive index which varies, the second phase shifter comprises a cell which shifts the phase of the light in compliance with the modulation signal, and the processor comprises a computer which samples and digitizes signals coming from the detector during the measuring window, calculates a fast Fourier transform (FFT) and determines a phase shift affecting a fundamental component of the intensity variations.

8. A device as claimed in claim 6, wherein:
the control which adjusts the period of the modulating signal combines respective signs of harmonic phases and a sign of the fundamental component in order to generate a correction signal.

9. A device as claimed in claim 7, wherein:
the control which adjusts the period of the modulating signal combines respective signs of harmonic phases and a sign of the fundamental component in order to generate a correction signal.

10. A device as claimed in claim 6, further comprising:
an automatic gain control which controls an amplification gain applied to signals produced by the photodetector.

11. A device as claimed in claim 7, further comprising:
an automatic gain control which controls an amplification gain applied to signals produced by the photodetector.

12. A device as claimed in claim 8, further comprising:
an automatic gain control which controls an amplification gain applied to signals produced by the photodetector.

13. A device as claimed in claim 9, further comprising:
an automatic gain control which controls an amplification gain applied to signals produced by the photodetector.

14. A device as claimed in claim 6, further comprising:
an amplifier which amplifies the signal from the photodetector, a generator which generates a periodic signal controlling the second phase-shifter, and wherein the processor calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

15. A device as claimed in claim 7, further comprising:
an amplifier which for amplifies the signal from the photodetector, a generator which generates a periodic signal controlling the second phase-shifter, and wherein the computer calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

16. A device as claimed in claim 8, further comprising:
an amplifier which amplifies the signal from the photodetector, a generator which generates a periodic signal controlling the second phase-shifter, and wherein the processor calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

17. A device as claimed in claim 9, further comprising:

an amplifier which for amplifies the signal from photodetector, a generator which generates a periodic signal controlling the second phase-shifter, and wherein the computer calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

18. A device as claimed in claim 10, further comprising:

an amplifier which amplifies the signal from the photodetector, a generator which generates a periodic signal controlling the second phase-shifter, and wherein the processor calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

19. A device as claimed in claim 11, further comprising:

an amplifier which for amplifies the signal from photodetector, a generator which generates a periodic signal controlling the second phase-shifter, and wherein the computer calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

20. A device as claimed in claim 12, further comprising:

an amplifier which amplifies the signal from the photodetector, a generator which generates a periodic signal controlling the second phase-shifter, and wherein the processor calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

21. A device as claimed in claim 13, further comprising:

an amplifier which for amplifies the signal from photodetector, a generator which generates a periodic signal controlling the second phase-shifter, and wherein the computer calculates a fast Fourier transform (FFT) on signals produced by the photodetector during a time interval, determines a phase shift affecting the fundamental component and delivers a first signal which controls a gain of the signal outputted by the photodetector and a second signal which controls a period of the modulating signal produced by a signal generator to be substantially equal to the duration of the time window.

22. A device as claimed in claim 14, wherein:

the processor combines respective signs of harmonic phases and a sign of the fundamental component to generate a correction signal.

23. A device as claimed in claim 15, wherein:

the processor combines respective signs of harmonic phases and a sign of the fundamental component to generate a correction signal.

24. A method as claimed in claim 1, wherein:

the two light beams are produced by interferential refractometry with the slower phase modulation being a result of a refractive index variation of a medium.

25. A device in accordance with claim 6 wherein:

the measurement of the phase shift is performed by calculating a complex fundamental component of the fundamental frequency.

26. A device in accordance with claim 7 wherein:

the measurement of the phase shift is performed by calculating a complex fundamental component of the fundamental frequency.

27. A device in accordance with claim 8 wherein:

the measurement of the phase shift is performed by calculating a complex fundamental component of the fundamental frequency.

28. A device in accordance with claim 9 wherein:

the measurement of the phase shift is performed by calculating a complex fundamental component of the fundamental frequency.

29. A device in accordance with claim 10 wherein:

the measurement of the phase shift is performed by calculating a complex fundamental component of the fundamental frequency.

30. A device in accordance with claim 11 wherein:

the measurement of the phase shift is performed by calculating a complex fundamental component of the fundamental frequency.

31. A device in accordance with claim 12 wherein:

the measurement of the phase shift is performed by calculating a complex fundamental component of the fundamental frequency.

32. A device in accordance with claim 13 wherein:

the measurement of the phase shift is performed by calculating a complex fundamental component of the fundamental frequency.

33. A device in accordance with claim 14 wherein:

the measurement of the phase shift is performed by calculating a complex fundamental component of the fundamental frequency.

34. A device in accordance with claim 14 wherein:

the measurement of the phase shift is performed by calculating a complex fundamental component of the fundamental frequency.

35. A device in accordance with claim 16 wherein:

the measurement of the phase shift is performed by calculating a complex fundamental component of the fundamental frequency.

36. A device in accordance with claim 17 wherein:

the measurement of the phase shift is performed by calculating a complex fundamental component of the fundamental frequency.

37. A device in accordance with claim 18 wherein:

the measurement of the phase shift is performed by calculating a complex fundamental component of the fundamental frequency.

38. A device in accordance with claim 19 wherein:

the measurement of the phase shift is performed by calculating a complex fundamental component of the fundamental frequency.

39. A device in accordance with claim 20 wherein:

the measurement of the phase shift is performed by calculating a complex fundamental component of the fundamental frequency.

40. A device in accordance with claim 21 wherein:

the measurement of the phase shift is performed by calculating a complex fundamental component of the fundamental frequency.

41. A device in accordance with claim 22 wherein:

the measurement of the phase shift is performed by calculating a complex fundamental component of the fundamental frequency.

42. A device in accordance with claim 23 wherein:

the measurement of the phase shift is performed by calculating a complex fundamental component of the fundamental frequency.

43. A device in accordance with claim 24 wherein:

the measurement of the phase shift is performed by calculating a complex fundamental component of the fundamental frequency.

\* \* \* \* \*